United States Patent [19]

Yamamoto et al.

[11] Patent Number: 4,908,353

[45] Date of Patent: Mar. 13, 1990

[54] NOVEL DIPEPTIDE USEFUL AS A PLANT GROWTH REGULATOR

[75] Inventors: Atsushi Yamamoto; Kazuharu Ienaga; Kunihiko Higashiura; Masaharu Kurohashi, all of Hyogo, Japan

[73] Assignee: Nippon Zoki Pharmaceutical Co., Ltd., Osaka, Japan

[21] Appl. No.: 257,605

[22] Filed: Oct. 14, 1988

[30] Foreign Application Priority Data

Oct. 16, 1987 [JP] Japan ................. 62-262437

[51] Int. Cl.$^4$ .................. A61K 37/02; C07K 5/06
[52] U.S. Cl. .................. 514/19; 562/553; 562/571
[58] Field of Search ............. 514/19; 562/553, 571

[56] References Cited

U.S. PATENT DOCUMENTS 3,683,019  8/1972  Wakamatsu et al. ........... 562/571
3,740,438  6/1973  Cook et al. ................... 514/19
3,857,879 12/1974  Abramitis ..................... 562/553
4,810,817  3/1989  Chmurny et al. .............. 562/571

Primary Examiner—Lester L. Lee
Attorney, Agent, or Firm—Armstrong, Nikaido, Marmelstein, Kubovcik & Murray

[57] ABSTRACT

The present invention relates to a novel dipeptide having the formula (I):

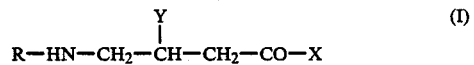

wherein R represents hydrogen atom or an amino-protecting group, Y represents hydrogen atom or hydroxy group which may optionally have protecting group, and X represents an acidic amino acid residue which may optionally have at least one protecting group; and pharmaceutical- acceptable salt thereof. These dipeptides are useful as plant growth regulator.

8 Claims, No Drawings

NOVEL DIPEPTIDE USEFUL AS A PLANT GROWTH REGULATOR

BACKGROUND OF THE INVENTION

The present invention relates to a novel dipeptide and a pharmaceutically acceptable salt thereof useful as a plant growth regulator.

Many attempts have been made to increase yield of agricultural products. The inventors of the present invention believed it was also important to prevent a decrease of agricultural yield resulting from abnormal environments. Therefore, they have searched for new compounds inducing resistance in plants against some kinds of stress, for example, compounds having a normalizing effect on the germination of low-temperature stressed plant. As a result of their earnest investigations, they have found the dipeptides of the present invention having excellent plant growth regulatory effect, and thus accomplished this invention.

An object of the present invention is to provide a novel dipeptide which has usefulness as a plant growth regulator.

DETAILED DESCRIPTION OF THE INVENTION

The novel dipeptide according to the present invention has the following formula (I):

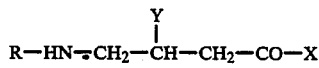
(I)

wherein R represents hydroqen atom or an amino-protecting group, Y represents hydrogen atom or hydroxy group which may optionally have protecting group, and X represents an acidic amino acid (i.e. glutamic acid or aspartic acid) residue which may optionally have at least one protecting group.

The dipeptides and amino acids in the present application are expressed by the abbreviations adopted by IUPAC and IUB or by the abbreviations commonly used in the art to which the present invention pertains. For example, the following abbreviations are used.

GABA: γ-aminobutyric acid
GABOB:γ-amino-β-hydroxybutyric acid
Glu: glutamic acid
Asp: aspartic acid In the above formula (I), X represents an acidic amino acid residue such as Glu, D-Glu, Asp or D-Asp which may optionally have protecting group. Preferred dipeptides of the present invention include GABA-Glu, GABA-D-Glu, GABA-Asp, GABA-D-Asp, GABOB-Glu, GABOB-D-Glu, GABOB-Asp, GABOB-D-Asp and the like. The protecting groups of a carboxy, amino or hydroxy group are described in detail as below.

The dipeptides according to the present invention can be produced by conventional processes in peptide chemistry, and either the solution method or the solid phase synthesis can be employed.

The coupling method for forming a peptide bond can include the azide method, active ester method, mixed acid anhydride method, acid chloride method, enzymatic coupling method, method employing a coupling reagent such as N,N'-dicyclohexylcarbodiimide (DCC), water-soluble carbodiimide (WSCD), N,N'-carbonyldiimidazole (CDI) and the like, or DCC-additive method wherein N-hydroxysuccinimide (HONSu), N-hydroxy-5-norbornene-2,3-dicarboxyimide (HONB), 1-hydroxybenzotriazole (HOBt) and the like can be employed as the additive.

An amino acid having an appropriate substituent group conventionally used in peptide chemistry can be employed as the starting material. Any side-chain groups and amino group which do not participate in the reaction can be protected by a known method, or any carboxy group or amino group which participates in the reaction can be activated.

As a protecting group of an amino group not participating in the condensation reaction, a protecting group conventionally employed in peptide synthesis chemistry can be used, i.e. a lower alkoxycarbonyl group such as t-butoxycarbonyl or t-pentoxycarbonyl group, an aralkyloxycarbonyl group such as benzyloxycarbonyl group, or an arakyloxycarbonyl group having substituent such as 0-chlorobenzyloxycarbonyl, p-nitrobenzyloxycarbonyl or p-methoxybenzyloxycarbonyl can be employed.

As a protecting group of carboxy group of acidic amino acid such as glutamic acid or aspartic acid residue, a protecting group conventionally employed in peptide synthesis chemistry can be used, i.e. an aralkyloxy group such as benzyloxy group, an aralkyloxy group having substituent such as p-methoxybenzyloxy group, lower alkoxy group such as t-butoxy or t-pentoxy group, cycloalkyloxy group such as cyclopentyloxy or cyclohexyloxy group, or piridiloxy group and the like.

The hydroxy group of GABOB may be optionally substituted by a hydroxy-protecting group conventionally employed in peptide synthesis chemistry can be used, i.e. aralkyl group such as benzyl group, an aralky group having substituent such as bromobenzyl or chlorobenzyl group, or a lower alkyl group such as t-butyl and the like.

These substituents can be removed by the conventional method such as catalytic reduction, acidolysis, etc.

In the above-mentioned coupling reaction and reaction removing substituents, the reaction temperature, reaction time and a kind of solvent can be appropriately determined according to conditions in conventional peptide syntheses.

The dipeptides of the present invention also include pharmaceutically acceptable salts of the compounds of the above formula (I) with alkali metal such as sodium, potassium, with alkaline earth metals such as calcium or barium, with other metals such as aluminium and the like, or with ammonia or organic amines.

The dipeptides of this invention can be include their metal complexes, for example complexes with zinc, nickel, cobalt, copper, iron etc.

These salts and metal complexes can be produced from free dipeptides in the usual way or can be interchanged with each other.

The amino acid residue in the present invention may be any of the D-isomer, L-isomer and DL-isomer.

EXAMPLE

The following examples, which are illustrative only and not intended to limit the scope of the invention, describe the preparation of the compounds of the present invention. The NMR was measured using t-butanol (δ=1.23 ppm) as the internal standard and expressed in the δ value, and the specific rotatory power was measured using sodium lump (λ=5893 Å).

In these examples, the following abbreviations of substituents or reagents are used.

Z: Benzyloxycarbonyl
OBzl: Benzyloxy
TosOH: Toluene sulfonic acid
EDC.HCl: 1-Ethyl-3-(3'-dimethylaminopropyl) carbodiimide hydrochloride

EXAMPLE 1.

(i) In 250 ml of dichloromethane, 11.9 g of Z-GABAOH, 26.5 g of TosOH.Glu(OBzl)-OBzl and 5.36 g of triethylamine were dissolved. 53 mmol of EDC.HCl was added to the solution in an ice-cold water, and the reaction mixture was stirred for 2 hrs at 0° C. and 20 hrs at room temperature. After the solvent was distilled off under reduced pressure, the residue was dissolved in a mixture of ethyl acetate and water, and the organic layer was separated. Ethyl acetate was added to the water layer and the organic layer was separated and combined with the layer of ethyl acetate obtained previously. The resulting organic layer was washed with 10% citric acid aqueous solution, water, 5% sodium hydrocarbonate aqueous solution and brine, and dried over anhydrous sodium sulfate. The solvent was distilled off under reduced pressure to give crude white crystals. The crystalline residue was purified by the use of silica gel column chromatography (ethyl acetate/chloroform=1/1) to give 17.4 g of Z-GABA-Glu(OBzl)OBzl.

Recovery: 64%
m.p.: 94°–95 ° C.
$[\alpha]^{20} = +1.0$ (C=1.0, CHCl$_3$)

In the same manner, the following compounds can be obtained.

Z-GABA-D-Glu(OBzl)-OBzl
Recovery: 69%
m.p.: 92°–93 ° C.
$[\alpha]^{20} = -1.1$ (c=1.0, CHCl$_3$)
Z-GABA-Asp(OBzl)-OBzl
Recovery: 70%
m.p.: 105°–106 ° C.
$[\alpha]^{20} = +15.4$ (c=1.0, CHCl$_3$)
Z-GABA-D-Asp(OBzl)-OBzl
Recovery: 70%
m.p.: 104–106 ° C.
$[\alpha]^{20} = -15.9$ (c=1.0, CHCl$_3$) Z-DL GABOB-Glu(OBzl)-OBzl (2) In a mixture of 200 ml of methanol, 50 ml of acetone and 10 ml of water, 17.4 g of Z-GABA-Glu(OBzl)-OBzl was dissolved, and hydrogenated in the presence of 10% palladium-carbon catalyst in the steam of hydrogen at atmospheric pressure at room temperature. After 20 hrs, the disappearance of the starting material was determined by the use of thin layer chromatography. The catalyst was filtered off and the solvent was distilled off under reduced pressure. Water and toluene were added to the oily residue and the remaining acetic acid was coevaporated off with the solvent under reduced pressure. The oily residue was crystallized from a mixture of water and ethanol to give 6.6 g of GABA-Glu (Compound 1) in the form of white powder.

Recovery: 89%
m.p.: 178°–180 ° C.
$[\alpha] = -4.9$ (c=1.0, H$_2$O)
Elementary Analysis: C$_9$H$_{16}$N$_2$O$_5$.0.2H$_2$O

|  | C % | H % | N % |
|---|---|---|---|
| Calculated | 45.84 | 7.01 | 11.88 |
| Found | 46.02 | 7.30 | 11.75 |

NMR (0.1 NDCl/D$_2$O): $\delta$=1.91–2.02(3H,m), 2.13–2.22(1H,m), 2.42(2H,t,J=7.5 Hz), 2.13–2.22(1H,m), 2.42(2H,t,J=7.5 Hz), 2.46(2H,t,J=7 Hz), 3.02(2H,t,J=7.5 Hz), 4.32(1H,dd,J=5, 9 Hz)

In the same manner, the following compounds can be obtained. GABA-D-Glu (compound 2)
Recovery: 86% m.p.: 175°–176 ° C.
$[\alpha]^{20} = +5.0$ (c=1.0, H$_2$O)
Elementary Analysis: C$_9$H$_{16}$N$_2$O$_5$.0.2 H$_2$O

|  | C % | H % | N % |
|---|---|---|---|
| Calculated | 45.84 | 7.01 | 11.88 |
| Found | 45.84 | 7.11 | 11.70 |

NMR (0.1 NDCl/D$_2$O): $\delta$=1.92–2.04(3H,m), 2.15–2.24(1H,m), 2.43(2H,t,J=7.5 Hz), 2.48(2H,t,J=7.0 Hz), 3.02(2H,t,J=7.5 Hz), 4.37(1H,dd,J=5, 9 Hz)
GABA-Asp (Compound 3)
Recovery: 92%
m.p.: 184°–185 ° C.
$[\alpha]^{20} = +11.7$ (c=1.0, $_2$O)
Elementary Analysis: C$_8$H$_{14}$N$_2$O$_5$

|  | C % | H % | N % |
|---|---|---|---|
| Calculated | 44.03 | 6.47 | 12.84 |
| Found | 44.13 | 6.79 | 12.50 |

NMR (0.1 NDCl/D$_2$O): $\delta$=1.95(2H,tt,J=7.5, 7.5 Hz), 2.43(2H,t,J=7.5 Hz), 2.93(1H,dd,J=7, 17 Hz), 2.98(1H,dd,J=5, 17 Hz), 3.01(2H,t,J=7.5 Hz), 4.77(1H,dd,5, 7 Hz)
GABA-D-Asp (Compound 4)
Recovery: 89% m.p.: 180°–182 ° C.
$[\alpha]^{20} = -11.0$ (c=1.0, H$_2$O)
Elementary Analysis: C$_8$H$_{14}$N$_2$O$_5$

|  | C % | H % | N % |
|---|---|---|---|
| Calculated | 44.03 | 6.47 | 12.84 |
| Found | 43.98 | 6.67 | 12.62 |

NMR (0.1 NDCl/D$_2$O): $\delta$=1.95(b 2H,tt,J=7.5, 7.5 Hz),
2.42(2H,t,J=7.5 Hz), 2.87(1H,dd,J=7, 17 Hz),
2.94(1H,dd,J=5, 17 Hz), 3.10(2H,t,J=7.5 Hz),
4.69(1H,dd,J=5, 7 Hz)
DL-GABOB-Glu (Compound 5)
NMR (0.1 NDCl/D$_2$O): $\delta$=1.95–2.06(1H,m), 2.17–2.26(1H,m),
2.47–2.53(2H,m), 2.54–2.58(2H,m), 2.96–3.03(1H,m), 3.16–3.22(1H,m), 4.23–4.31(1H,m), 4.40–4.46(1H,m)

The plant growth regulatory effects of the compounds of the present invention are described below.
1. Rice germination test The filter paper soaked with an aqueous solutions of a test drug (1×10$^6$M) was laid in a germination dish. The germination dish was seeded with rice (*Oryza sativa L. japonica*). The seeds were treated with the aqueous solution of the test drug only during the germination period (4 days). Lengths and weights of both shoots and roots were measured 7 days after transplantation from the germination dish to a water culture vessel not containing any test drug. These tests was carried out in a dark room at 20° C. and results of t-test between a control group and a test group are indicated thus; *p<0.001, p<0.01, *p<0.05; n=30. The results are shown in Table 1 and 2.

TABLE 1

| Test Drug | Shoot length (mm) | Root length (mm) |
|---|---|---|
| control | 44.9 ± 0.98 | 49.2 ± 2.70 |
| Compound 1 | 55.8 ± 1.02*** | 61.5 ± 2.83** |
| Compound 2 | 55.5 ± 1.08*** | 55.2 ± 4.67 |
| Compound 3 | 57.1 ± 0.89*** | 63.3 ± 3.32** |
| Compound 4 | 54.8 ± 0.91*** | 66.8 ± 3.34*** |

TABLE 2

| Test Drug | Shoot weight (mg) | Root weight (mg) |
|---|---|---|
| control | 21.4 ± 0.58 | 23.6 ± 1.89 |
| Compound 1 | 26.1 ± 0.71*** | 30.8 ± 1.23** |
| Compound 2 | 26.1 ± 0.98** | 30.0 ± 0.74* |
| Compound 3 | 25.2 ± 0.77** | 24.6 ± 1.28 |
| Compound 4 | 24.5 ± 0.66** | 28.3 ± 1.86 |

As apparently shown by the above-mentioned results, the dipeptides of the present invention have excellent plant growth regulatory effects. Significant effects of the present dipeptides were observed on inhibited plant growth at low temperature (20° C.), in comparison with the optimum temperature (30° C.). Namely, the compounds of this invention have normalizing effects on the germination of low-temperature stressed plant.

In addition, the plant growth regulatory effect of the present dipeptide can be taken by the treating seeds with drug solution only during the germination period, preferably $1 \times 10^{-4}$M to $1 \times 10^{-10}$M solution, therefore, it is very easy to use and advantageous economically. The dipeptides of the present invention are very useful as plant growth regulator.

We claim:

1. A dipeptide having the formula (I):

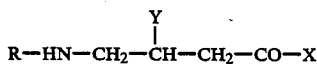

(I)

wherein R represents a hydrogen atom or an amino-protecting group selected from the group consisting of t-butoxycarbonyl, t-pentoxycarbonyl, benzyloxycarbonyl, o-chlorobenzyloxycarbonyl, p-nitrobenzyloxycarbonyl and p-methoxybenzyloxycarbonyl, Y represents hydrogen atom or hydroxy group having a protecting group selected from the group consisting of benzyl, bromobenzyl, chlorobenzyl and t-butyl, and X represents glutamic acid or aspartic acid which may optionally have at least one protecting group selected from the group consisting of benzyloxy, p-methoxybenzyloxy, t-butoxy, t-pentoxy, cyclopentyloxy, cyclohexyloxy and piridiloxy;

and pharmaceutical acceptable salts thereof.

2. A dipeptide having the formula (I'):

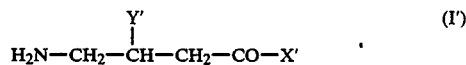

(I')

wherein Y' represents hydrogen atom or hydroxy group, and X' represents glulamic acid or aspartic acid; and pharmaceutical acceptable salt thereof.

3. A dipeptide or pharmaceutical acceptable salt thereof according to claim 2 wherein Y is hydrogen atom.

4. A dipeptide or pharmaceutical acceptable salt thereof according to claim 2 wherein Y is hydroxy group.

5. A dipeptide or pharmaceutical acceptable salt thereof according to claim 3 or claim 4 wherein X is glutamic acid.

6. A dipeptide or pharmaceutical acceptable salt thereof according to claim 3 or claim 4 wherein X is aspartic acid.

7. A dipeptide or pharmaceutical acceptable salt thereof according to claim 2 which is γ-aminobutyryl-glutamic acid, γ-aminobutyryl-D-glutamic acid, γ-aminobutyryl-aspartic acid, γ-aminobutyryl-D-aspartic acid, γ-amino-β-hydroxybutyryl-glutamic acid, γ-amino-β-hydroxybutyryl-D-glutamic acid, γ-amino-β-hydroxybutyryl-aspartic acid or γ-amino-62-hydroxybutyryl-D-aspartic acid.

8. A plant growth regulator composition comprising as an active ingredient an effective amount of at least one dipeptide of the formula (I):

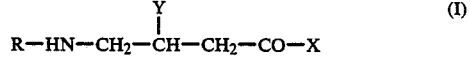

(I)

wherein R represents a hydrogen atom or an amino-protecting group selected from the group consisting of t-butoxycarbonyl, t-pentoxycarbonyl, benzyloxycarbonyl, o-chlorobenzyloxycarbonyl, p-nitrobenzyloxycarbonyl and p-methoxybenzyloxycarbonyl, Y represents hydrogen atom hydroxy group having a protecting group selected from the group consisting of benzyl, bromobenzyl, chlorobenzy and t-butyl, and X represents glutamic acid or aspartic acid which may optionally have at least one protecting group selected from the group consisting of benzyloxy, p-methoxybenzyloxy, t-butoxy, t-pentoxy, cyclopentyloxy, cyclohexyloxy and piridiloxy;

and pharmaceutical acceptable salts thereof.

* * * * *